(12) United States Patent
Prasad

(10) Patent No.: US 10,358,620 B2
(45) Date of Patent: Jul. 23, 2019

(54) AMINOALCOHOL SALTS OF ALKYLBENZENE SULFONIC ACIDS AND THEIR USE IN DETERGENT FORMULATIONS

(71) Applicant: Dow Global Technologies LLC, Midland, MI (US)

(72) Inventor: Vikram Prasad, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 12 days.

(21) Appl. No.: 15/548,426

(22) PCT Filed: Mar. 17, 2016

(86) PCT No.: PCT/US2016/022849
§ 371 (c)(1),
(2) Date: Aug. 3, 2017

(87) PCT Pub. No.: WO2016/175932
PCT Pub. Date: Nov. 3, 2016

(65) Prior Publication Data
US 2018/0037847 A1 Feb. 8, 2018

Related U.S. Application Data

(60) Provisional application No. 62/155,042, filed on Apr. 30, 2015.

(51) Int. Cl.

| | | |
|---|---|---|
| *C11D 1/22* | (2006.01) | |
| *C07C 309/31* | (2006.01) | |
| *C11D 3/30* | (2006.01) | |
| *C11D 10/04* | (2006.01) | |
| *C11D 17/04* | (2006.01) | |
| *C07C 215/08* | (2006.01) | |
| *C07C 215/10* | (2006.01) | |

(52) U.S. Cl.
CPC ............. *C11D 1/22* (2013.01); *C07C 215/08* (2013.01); *C07C 215/10* (2013.01); *C07C 309/31* (2013.01); *C11D 3/30* (2013.01); *C11D 10/04* (2013.01); *C11D 17/042* (2013.01)

(58) Field of Classification Search
None
See application file for complete search history.

(56) References Cited

U.S. PATENT DOCUMENTS

| | | | |
|---|---|---|---|
| 4,266,962 A | 5/1981 | Kersting et al. | |
| 4,973,416 A | 11/1990 | Kennedy | |
| 8,835,374 B2 | 9/2014 | Guida et al. | |
| 2006/0275566 A1 | 12/2006 | de Buzzaccarini et al. | |
| 2008/0146482 A1 | 6/2008 | Schneiderman et al. | |
| 2011/0061174 A1 | 3/2011 | Boutique et al. | |
| 2013/0196893 A1* | 8/2013 | Busby | C11D 3/30 510/499 |
| 2015/0376556 A1* | 12/2015 | Ohtani | C11D 17/043 510/386 |
| 2017/0335240 A1* | 11/2017 | Della Noce | C11D 1/83 |

FOREIGN PATENT DOCUMENTS

| | | |
|---|---|---|
| CS | 251132 | 6/1987 |
| EP | 107023 | 5/1984 |
| FR | 1387902 | 2/1965 |
| WO | 2002060758 | 8/2002 |
| WO | 2004031481 | 4/2004 |
| WO | 2011094470 | 8/2011 |

OTHER PUBLICATIONS

Concentrated alkylbenzene sulfonate alkanolammonium salts and their use in detergent compositions, IP.com Journal, vol. 9, Issue 3A, p. 22 (2009).

* cited by examiner

*Primary Examiner* — Necholus Ogden, Jr.
(74) *Attorney, Agent, or Firm* — Thomas S. Deibert

(57) ABSTRACT

Provided are amine-neutralized anionic surfactants and their use in detergent formulations. The amine-neutralized anionic surfactants are of the formula I, as described herein.

4 Claims, No Drawings

AMINOALCOHOL SALTS OF ALKYLBENZENE SULFONIC ACIDS AND THEIR USE IN DETERGENT FORMULATIONS

CROSS-REFERENCE TO RELATED APPLICATIONS

This application claims priority from U.S. provisional application Ser. No. 62/155,042, filed Apr. 30, 2015, which is incorporated herein by reference in its entirety.

FIELD

This invention relates generally to alkylbenzene sulfonic acid surfactants, more particularly alkylbenzene sulfonic acid surfactants neutralized with certain amine compounds, and their use in detergent formulations.

BACKGROUND

Recent commercial innovations in the liquid laundry detergent market include "unit dose" products, where detergent components are placed within a water-soluble polymer pouch. These unit dose products are characterized by high actives concentration, and low water content (typically less than 15%). In order to create such high active formulations, surfactants molecules are required that can exist in such compact spaces without causing adverse effects to formulation stability. Some of these adverse effects include increase in viscosity of the formulation, and interactions of the formulation with the encasing polymer (in most cases polyvinyl alcohol (PVOH)), resulting in undesirable gel blobs or undispersed flocs.

Current formulations generally contain one or more surfactants, typically anionic and/or nonionic surfactants or combinations thereof. A commonly used class of anionic surfactants are the linear alkylbenzene sulfonic acids ("HLAS").

The acid group of HLASs is neutralized with various bases to obtain functioning surfactants (at about pH 7 or so). Some common examples of bases that are used in commercial surfactant applications are NaOH (giving LABS linear alkylbenzene sulfonate sodium salt). Known neutralized HLASs, such as LABS, however, are lacking in a number of areas. For instance, such compounds may exhibit the disadvantages indicated above, including undesirably high viscosity when formulated in a detergent composition, and/or formation of gel blobs or undispersed flocs resulting from interaction with the PVOH film.

The problem addressed by this invention is the provision of new alkylbenzene sulfonic acid salts that address various shortcomings of existing materials.

STATEMENT OF INVENTION

We have now found that alkylbenzene sulfonic acids can be neutralized with certain aminoalcohol compounds, as described herein, to provide surfactants with favorable properties. Advantageously, in some embodiments, the surfactants of the invention exhibit lower viscosity compared to conventional surfactants, such as linear alkylbenzene sulfonic acid, sodium salt or monoethanolamine salt. The surfactants also interact with PVOH film differently from conventional linear alkylbenzene sulfonic acid based surfactants, and can allow for higher water content in unit dose detergent formulations. Further, various surfactants of the invention, when present in unit dose formulations, can mitigate or lower floc formation when interacting with PVOH solutions.

In one aspect, there is provided an amine-neutralized anionic surfactant of formula I:

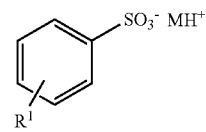
(I)

wherein $R^1$ is $C_4$-$C_{14}$ alkyl, and M is an aminoalcohol compound of formula II:

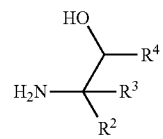
(II)

wherein $R^2$ is $C_1$-$C_6$ alkyl or $CH_2OH$; $R^3$ is H or $CH_2OH$; and $R^4$ is H or $C_1$-$C_6$ alkyl.

In another aspect, there is provided a detergent packet comprising a detergent formulation containing an amine-neutralized anionic surfactant as described herein encased in a water soluble polyvinyl alcohol pouch.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight. Weight percentages (or wt %) in the compositions are percentages of dry weight, i.e., excluding water that may be present in the composition.

"Alkyl," as used in this specification encompasses linear and branched chain aliphatic groups having the indicated number of carbon atoms. Preferred alkyl groups include, without limitation, methyl, ethyl, propyl, isopropyl, butyl, isobutyl, sec-butyl, tert-butyl, pentyl, and hexyl.

As indicated above, in one aspect, the invention provides an amine-neutralized anionic surfactant of formula I:

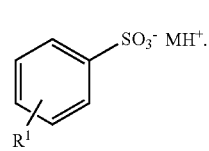
(I)

$R^1$ in the formula 1 compound is $C_4$-$C_{14}$ alkyl (linear or branched). In some embodiments, $R^1$ may be linear $C_4$-$C_{14}$ alkyl. In some embodiments, $R^1$ may be linear $C_{10}$-$C_{13}$ alkyl.

MH+ in formula I is an aminoalcohol compound, forming the counterion of the neutralized alkylbenzene sulfonate component of formula I. M, the aminoalcohol compound, is of formula II:

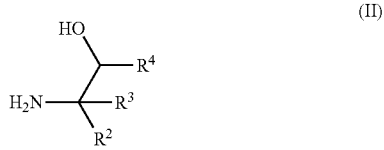

wherein $R^2$ is $C_1$-$C_6$ alkyl or $CH_2OH$; $R^3$ is H or $CH_2OH$; and $R^4$ is H or $C_1$-$C_6$ alkyl.

In some embodiments, $R^2$ is methyl, ethyl, or n-propyl, preferably it is ethyl. In some embodiments, $R^2$ is $CH_2OH$.

In some embodiments, $R^3$ is H. In some embodiments, $R^3$ is $CH_2OH$.

In some embodiments, $R^4$ is H. in some embodiments, $R^4$ is ethyl, n-propyl, or n-butyl, preferably n-butyl.

Preferred compounds of formula II include 3-amino-4-octanol and 2-amino-2-hydroxymethyl-1,3-propanediol.

Compounds of formula II are commercially available and/or they may be synthesized by those skilled in the art using literature methods.

Compounds of formula I may be readily prepared by mixing in water and/or other solvents an alkylbenzene sulfonic acid with the aminoalcohol compound of formula II. Mixing may typically be conducted at room temperature using, for example, a mechanical or magnetic stirrer. Additional details are provided by the Examples.

Preferred compounds of formula I include:

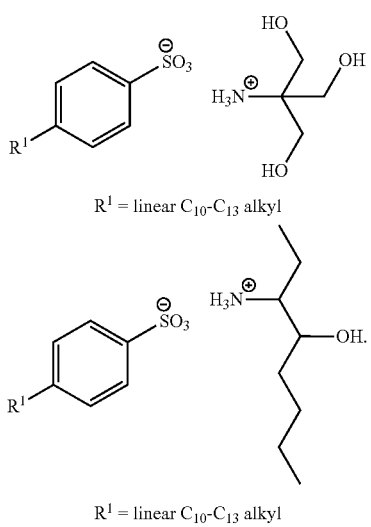

The amine neutralized anionic compounds of formula I are useful as surfactants in a wide variety of applications. Preferably, the compounds are useful in detergent formulations for cleaning, such as in laundry detergents. More preferably, they are used in unit dose, or sealed package detergent forms. Preferably, the sealed package containing the detergent formulation is added to a washing machine. The amount of amine-neutralized anionic surfactant of formula I used in a detergent formulation may, for instance, be at least 20 wt %, alternatively at least 24 wt %, and up to 40 wt %, alternatively up to 32 wt %, based on the total weight of the detergent formulation.

When used in a detergent formulation for a detergent packet, such detergent formulation may contain various additional ingredients. For instance, the formulation may contain one or more fatty acid salts (created by neutralization with fatty acids), one or more additional surfactants, one or more solvents (e.g., propylene glycol and glycerol) and water.

Suitable fatty acids for the salts include, without limitation, distilled palm kernel fatty acids (such as PALMERA B1220). The amount of fatty acid in the detergent formulation may, for instance, be from 4.5 to 5.5 percent by weight, based on the total weight of the detergent formulation.

Additional surfactants may be included in the detergent formulation. The surfactant(s) may be cationic, anionic, nonionic, fatty acid salt, zwitterionic or betaine surfactants. Preferably, the detergent formulation comprises at least one anionic surfactant, preferably at least two. One or both of the anionic surfactants maybe amine-neutralized anionic surfactants of formula I.

Preferably, the optional nonionic surfactants have an alkyl group having at least eight carbon atoms and at least five polymerized ethylene oxide or propylene oxide residues. Preferably, nonionic surfactants have at least five polymerized ethylene oxide residues, preferably at least six, preferably at least seven; preferably no more than twelve, preferably no more than eleven, preferably no more than ten. Preferably, the detergent composition comprises at least 5 wt % linear alcohol ethoxylates, preferably at least 6 wt %, preferably at least 8 wt %; preferably up to 22 wt %. Preferably, a linear alcohol ethoxylate has a C8-C18 alkyl group, preferably C10-C16, preferably C12-C15. Preferably, a linear alcohol ethoxylate contains from six to twelve polymerized units of ethylene oxide, preferably from seven to ten. Preferably, anionic surfactants have an alkyl group having at least ten carbon atoms and an anionic group, preferably selected from sulfonates and sulfates. Anionic surfactants also may have polymerized residues of ethylene oxide, and/or may have aromatic rings, e.g., linear alkylbenzene sulfonates. Some anionic surfactants are fatty acid salts. Preferably, the detergent composition comprises no more than 25 wt %, alternatively no more than 15 wt %, alternatively no more than 5 wt %, alternatively no more than 3 wt %, or alternatively no more than 1 wt %, of linear alkylbenzene sulfonates (separate from the amount contributed by the amine-neutralized anionic surfactant of formula I). Preferably, alkylbenzene sulfonates, besides those of formula I, if present, have a C10-C14 alkyl group.

Preferably, the detergent composition comprises at least 2 wt % alkyl sulfates, preferably at least 3 wt %, preferably at least 4 wt %. Preferably, the detergent composition comprises no more than 15 wt % alkyl sulfates, preferably no more than 13 wt %. Preferably, an alkyl sulfate contains from one to five polymerized ethylene oxide units per molecule.

The detergent formulation may contain one or more non-aqueous solvents. Suitable non-aqueous solvents include, without limitation, propylene glycol and glycerol. The amount of each non-aqueous solvent, such as propylene glycol and glycerol, may, for instance, be from 5 wt % to 20 wt %.

The detergent formulation may contain water, although typically the amount is less than 20 wt %, alternatively less than 15 wt %, and maybe at least 1 wt %, alternatively at least 4 wt %.

Preferably, the pH of the detergent formulation is from 4 to 11, preferably from 4.5 to 10, preferably from 4.5 to 9, preferably from 6 to 8. Suitable bases to adjust the pH of the formulation, if needed, include mineral bases such as sodium hydroxide and potassium hydroxide; ammonium hydroxide; and organic bases such as mono-, di- or triethanolamine; or 2-dimethylamino-2-methyl-1-propanol (DMAMP). Mixtures of bases may be used. Suitable acids to adjust the pH of the formulation, if needed, include mineral acids such as hydrochloric acid, phosphorus acid, and sulfuric acid; and organic acids such as acetic acid. Mixtures of acids may be used. The formulation may be adjusted to a higher pH with base and then back titrated to the ranges described above with acid.

When used as unit dose detergent packages, the detergent formulation is generally encased and sealed within a polyvinyl alcohol (PVOH) pouch. Methods for forming such pouches are known and are described in, for instance, WO 2002/060758A1. The amount of detergent formulation in a pouch may vary depending on the size of the package desired. The amount may, for instance, range from 3 g to 35 g.

Some embodiments of the invention will now be described in detail in the following Examples.

Preparation of Surfactant Solutions

Monoethanolamine (MEA): In a 110 mL glass bottle, add 56.7 g of de-ionized water. Under agitation with a magnetic stir bar, add 3.16 g of MEA until completely solubilized. Then, slowly add in linear alkylbenzene sulfonic acid (alkyl is about C10-C13 in the para position of the phenyl ring) (HLAS) in a drop-wise fashion, all the while under agitation. Continue till the mass of HLAS added is 15.08 g. Continue agitating till all the components (HLAS+MEA) are fully solubilized and no visible particulates or aggregates are observed. The total surfactant concentration is calculated to be (3.16+15.08)*100/(3.16+15.08+56.7)=24.3%. The pH of the solution is then measured, which in this instance is pH=8.27

Surfactant solutions: The above example is used to estimate how to create surfactant solutions with the aminoalcohols. A solution with 2-amino-2-hydroxymethyl-1,3-propanediol is prepared as follows. In a 110 mL glass bottle, add 52.5 g of de-ionized water. Under agitation, add 7.12 g of 2-amino-2-hydroxymethyl-1,3-propanediol until completely solubilized. Then, slowly add 15.38 g of HLAS in a drop-wise fashion and continue agitating till no visible particulates or aggregates are observed. The total surfactant concentration is calculated to be 30 wt %, and the pH of the solution is 7.95.

3-Amino-4-octanol based surfactants are not soluble in water by themselves, and require the addition of propylene glycol.

Detergent Formulations:

In addition to the surfactants solutions as described above, detergent formulations are prepared containing two solvents (propylene glycol and glycerol), two surfactants (BIOSOFT N25-7, a linear alcohol ethoxylate with 7 moles EO and STEOL CS270, an alkyl ether sulfate with 2 moles EO from Stepan) and a fatty acid (PALMERA B1220 from Croda). A typical example for preparation of such detergent formulation is as follows:

In a 110 mL glass bottle, add 2 g of de-ionized water to 7.5 g of propylene glycol and mix with a magnetic stir bar. Then, slowly add 7 g of STEOL CS 270, followed by 9 g of BIOSOFT N 25-7. Continue mixing until the two surfactants are fully soluble and no aggregates are visible. Subsequently, add 2 g of PALMERA B1220 and 2.75 g glycerol while stirring, and wait till fully solubilized. For the final neutralization step, mix 2.1 g of MEA into solution. Then, slowly add HLAS in a drop-wise fashion under agitation, and continue till the mass of HLAS added is 7.5 g. Allow all components of solution to be completely soluble, and let the solution stand overnight. Measure the pH of the solution, and adjust by adding MEA if necessary.

The following examples demonstrate the advantages of the surfactants of the invention over conventional LAS-Na and HLAS-MEA surfactants.

Viscosity

The viscosities of the surfactant solutions (2-amino-2-hydroxymethyl-1,3-propanediol, Na salt, and MEA) prepared as described in the previous section are measured with a Brookfield viscometer, at shear rates between 6 and 60 s−1. The data are shown in Table 1

TABLE 1

| Surfactant | Viscosity (cps) |
|---|---|
| LAS-MEA (comparative) 24.3 wt % | 2920 |
| LAS-Na (comparative) 24.6 wt % | 611 |
| LAS-2-amino-2-hydroxymethyl-1,3-propanediol (inventive) 30 wt % | 549 |

The data in Table 1 indicates that on a molar basis (that is, same number of molecules per unit volume), surfactants of the invention show superior viscosity compared to the Na or MEA salts.

Interactions with PVOH

In this Example, approximately 0.6 g of PVOH film (M8630, commercially obtained from Monosol Inc.) is added to 6 g of 20 wt % surfactant solutions and vigorously shaken by hand. With the MEA-based surfactant, used commonly in many commercial liquid laundry formulations, the PVOH film interacts with the surfactant/water mixture to form a 'glob,' i.e., a not fully solubilized complex. For the 2-amino-2-hydroxymethyl-1,3-propanediol based surfactant solution, on the other hand, the PVOH film is completely solubilized (to a lesser extent, this is true for the LAS-Na surfactant solution as well). For the 3-amino-4-octanol based surfactant, the PVOH film did not interact with the surfactant solutions and was largely intact.

Interactions with Water

In this Example, 1.5 g of detergent formulation is added to 1.5 g of de-ionized water in a vial which is vigorously hand shaken. Formulations containing MEA-based and 2-amino-2-hydroxymethyl-1,3-propanediol based surfactants form viscous aggregates. In contrast, formulations containing 3-amino-4-octanol exhibit lower viscosity and are homogeneous when water is added.

Interactions of Complex Formulations with PVOH

In this Example, 3 g of detergent formulation is added to 0.6 g of a 10 wt % PVOH solution (prepared by dissolving PVOH film in water). This example mimics dynamically what happens when a pouch is dissolved in water, first the PVOH film dissolves in the water, and then the formulation contents are released in the wash. Interactions then take place between the formulation components, water, and dissolved PVOH.

Undissolved flocs are clearly visible in all the vials. The flocs have a quasi-regular shape (ellipsoidal), allowing for estimation of floc size based on their dimensions. The diminishing order of floc appearance is as follows (ranked against MEA with a size index of 100): 2-amino-2-hydroxymethyl-1,3-propanediol (104), MEA (100), 3-amino-4-octanol (75).

This test indicates that 3-amino-4-octanol can lower the size of flocs formed with PVOH in the presence of water and other formulation components, compared to MEA.

What is claimed is:

1. A unit dose laundry detergent package comprising: a water soluble polyvinyl alcohol pouch, and
a detergent formulation,
wherein the detergent formulation is encased in the water soluble polyvinyl alcohol pouch; and
wherein the detergent formulation comprises 24 to 40 wt % of an amine-neutralized anionic surfactant of formula I:

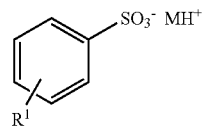

wherein $R^1$ is $C_4$-$C_{14}$ alkyl, and M is an aminoalcohol compound which is 2-amino-2-hydroxymethyl-1,3-propanediol.

2. The surfactant of claim 1, wherein R1 is in the 4-position of the phenyl ring.

3. The surfactant of claim 1, wherein R1 is liner C10-C13 alkyl.

4. The detergent packet of claim 1, wherein R1 the detergent formulation further comprises fatty acid salts, one or more additional surfactants, one or more solvents and water.

* * * * *